United States Patent [19]

Berner et al.

[11] Patent Number: 5,798,839

[45] Date of Patent: Aug. 25, 1998

[54] METHOD FOR DETERMINING THE COLOR STIMULUS SPECIFICATION OF TRANSLUCENT OBJECTS AND AN APPARATUS FOR PERFORMING THE METHOD

[75] Inventors: Markus Berner, Niederhalsi, Switzerland; Carlo Gobbetti, Verona, Italy

[73] Assignee: MHT Optic Research AG, Niederhasli, Switzerland

[21] Appl. No.: 758,919

[22] Filed: Dec. 2, 1996

[30] Foreign Application Priority Data

Dec. 1, 1995 [CH] Switzerland ............... 3405/95

[51] Int. Cl.$^6$ .............. G01N 21/27; G01N 21/49
[52] U.S. Cl. .............. 356/402; 356/405; 356/446
[58] Field of Search ............... 356/326, 319, 356/402, 405, 445, 446

[56] References Cited

U.S. PATENT DOCUMENTS 5,428,450  6/1995  Vieillefosse et al. ............ 356/405
5,471,311  11/1995  Van Den Bergh et al. ............ 356/446

Primary Examiner—Vincent P. McGraw
Attorney, Agent, or Firm—Tarolli, Sundheim, Covell, Tummino & Szabo

[57] ABSTRACT

The apparatus for determining the color stimulus specification of translucent objects comprises two light sources to create on the surface of an object under test two light spots which have different size. The light is transmitted from the light sources to the object under test by means of an optically conducting fiber bundle. The light reflected by the object under test is received by a lens and led via an optically conducting fiber bundle to a spectrometer. Thereafter, the measurement signal is digitized and arithmetically evaluated in a microprocessor. Due to the fact that two differently sized light spots are used, the measurement error which results in determining the color specification value of a translucent object can be defined and corrected. For this purpose, use is made of reference measurement values which have been obtained by measuring opaque reference objects and which have been stored in a memory module of the apparatus. In order to eliminate the influence of the disturbing ambient light, a further measurement without any light spot can be performed.

22 Claims, 4 Drawing Sheets

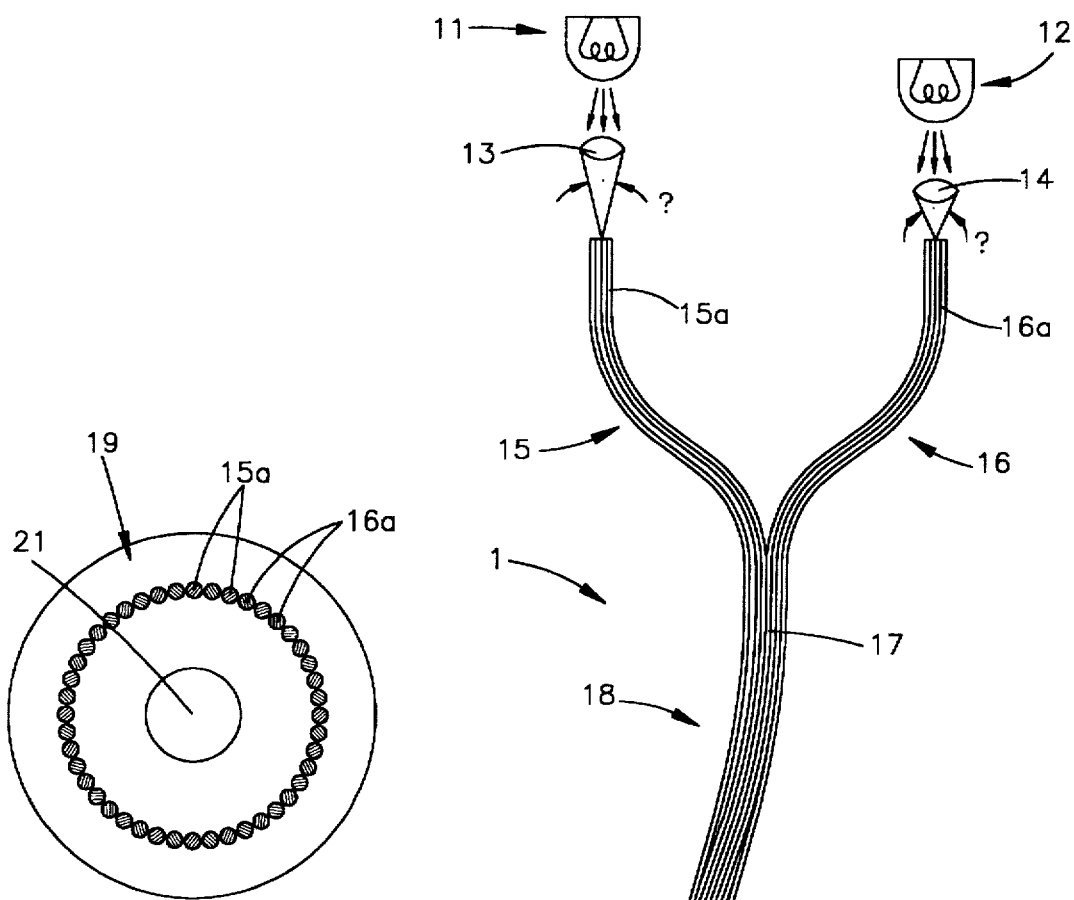
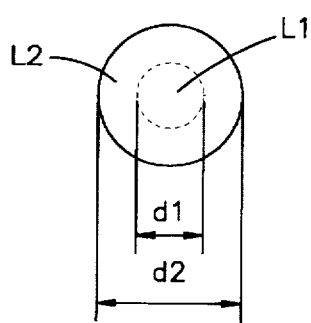
Fig.2a
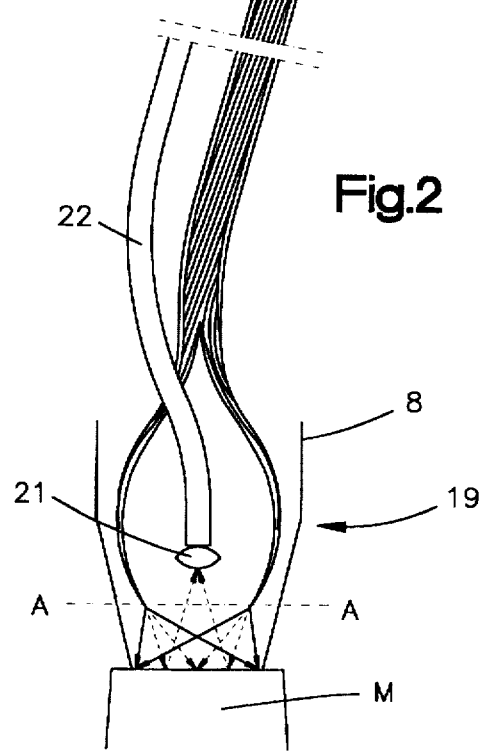
Fig.2b
Fig.2

METHOD FOR DETERMINING THE COLOR STIMULUS SPECIFICATION OF TRANSLUCENT OBJECTS AND AN APPARATUS FOR PERFORMING THE METHOD

FIELD OF THE INVENTION

The present invention refers to a method for determining the color stimulus specification of translucent objects, in which the surface of the object under test is partially illuminated and the light reflected by a selected portion of the surface of the object under test is measured and arithmetically evaluated. Moreover, the invention refers to an apparatus for determining the color stimulus specification of translucent objects, comprising a light source for illuminating the object under test, an optical receiver for receiving the light reflected by the object under test which is illuminated by the light source, a sensor for measuring the light received by the optical receiver, and a microprocessor for evaluating the measurement data.

BACKGROUND OF THE INVENTION

The determination of the hue or tint of translucent objects is a process which is frequently performed in the field of dentistry. In practice, it is necessary to select that denture out of a number of sample dentures which matches the hue or tint of the tooth to be replaced. Frequently, instead of determining the color of the tooth to be replaced, the hue or tint of the adjacent tooth or of the two adjacent teeth is determined.

The manufacturers of basic materials for the production of a denture can supply assortments comprising a plurality of sample dentures having different hue or tint; each denture of such an assortment has an allocation number by which the hue or tint of the denture is exactly specified. If a dentist has to produce a denture, up to now he proceeds, simply expressed, as follows:

He visually compares the color of the tooth to be replaced with the color of the dentures provided in an assortment and selects that denture of the assortment which matches the color of the tooth to be replaced most closely. On the basis of the allocation number of the selected denture, the dentist knows the exact specification of the materials needed to produce a denture with the same hue or tint and he is in a position to manufacture the required individual denture. However, this proceeding is, on the one hand, quite lavish and can lead, on the other hand, to errors as far as the hue or tint of the final denture is concerned.

PRIOR ART

Methods and apparatuses are known in the art to determine the color stimulus specification of translucent objects. In these methods and apparatuses, the object to be tested and a portion thereof, respectively, is illuminated by a light spot, and the light reflected by a predetermined area, called measurement spot, is measured and subsequently evaluated. But due to the fact that neither the measurement spot nor the light spot projected onto the surface of the object under test are infinitely large and theoretically cannot be infinitely large, a measurement error results in practice. The reasons for this measurement error, on the one hand, is that a part of the light leaves the measurement spot through the interior of the translucent object, and on the other hand, that a certain amount of light penetrates through the translucent object and further illuminates the measurement spot. In other words, because the luminous flux leaving the translucent object to be tested is not equal to the luminous flux which is coupled from the exterior into the measurement spot and which is received by the receiving element, the measuring result is distorted in dependence of the translucency of the object under test.

The above mentioned measurement error leads to the fact that the color stimulus specification of unknown translucent objects cannot be measured with sufficient accuracy with the help of the systems known up to now.

The European Patent Publication No. 0,250,519 discloses a method and an apparatus for determining the color of an object, particularly of a denture. The apparatus essentially comprises a spectro-colorimeter, a microprocessor, a light source, a light receiving instrument and an assembly of photo cells. Two light emitting diodes are provided for the internal calibration of the apparatus and the photo cells, respectively; the wave lengths of the light emitted by the two LED's are different from each other. The light receiving instrument serves for illuminating the object as well as for measuring the light reflected by the object under test. For this purpose, the light receiving instrument is provided with a cylindrically shaped head in which two light conductors are inserted, located one next to each other. One of the light conductors serves for illuminating the object under test, while the other light conductor is used for measuring the light reflected by the object under test. The reflected light is led by the light conductor to the spectro-colorimeter by means of which the diffuse spectral reflection of the tooth is measured. In order to define the color of the denture, thereafter, the trichromatic color proportions at different illumination conditions are calculated.

In practice, it has shown that the color determination of the denture, performed with the help of such an apparatus, is not sufficiently accurate as far as the optical feeling of the human is concerned. The reasons therefor most probably are the same as discussed herein before, i.e. the problems which are encountered in determining the color stimulus specification of translucent objects, because the artificial teeth (dentures) do not show exactly the same translucency as natural human teeth. Due to the asymmetrical design of the light receiving instrument, as far as the light emitting light conductor and the light receiving light conductor are concerned, further error possibilities are generated which distort the final measurement result. In fact, different measuring results can obtained, depending on the angle on which the light hits the surface of the tooth.

OBJECTS OF THE INVENTION

It is an object of the invention to provide a method for determining the color stimulus specification of translucent objects by means of which the color stimulus specification of translucent objects can be determined with greater accuracy.

It is a further object of the invention to provide an apparatus for determining the color stimulus specification of translucent objects by means of which the color stimulus specification of translucent objects can be determined with greater accuracy and which can be operated easily and quickly.

SUMMARY OF THE INVENTION

In order to meet these and other objects, the inventions provides, according to a first aspect, a method for determining the color stimulus specification of translucent objects, in which the surface of the object under test is partially illuminated and the light reflected by a selected portion of the surface of the object under test is measured and arithmetically evaluated. Basically the method according to the invention can be performed in three similar, but slightly different ways. Thereby, in each case, the real method steps are identical, i.e.:

(i) in a first measurement, a first portion of the surface of the object under test having a first area is illuminated, and the light reflected by a second portion of the surface of the object under test having a second area is measured. Thus, a first set of measurement values is obtained;

(ii) in a second measurement, a third portion of the surface of the object under test having a third area is illuminated, and the light reflected by a fourth portion of the surface of the object under test having a fourth area is measured. Thus a second set of measurement values is obtained;

(iii) on the basis of a set of reference measurement values obtained from the measurement of a reference object, first and second sets of compensated measurement values are calculated. The first and second sets of compensated measurement values are functions of the first and second sets of measurement values and the reference measurement values;

(iv) then, an intermediate reflection value is calculated as a function of the first and second sets of compensated measurement values and a correction value which corresponds to the light loss caused by the translucency of the object under test; and (v) a final reflection value is calculated as a function of the intermediate reflection value and the known reflection values of the reference object to obtain from the final reflection value the color stimulus specification of the object under test.

The difference between the afore mentioned three possibilities is, that according to a first possibility, the first area of the first portion and the third area of the third portion are equal in size, and the fourth area of the forth portion has a size which is different from the size of the second area of the second portion;

according to a second possibility, the third area of the third portion has a size which is different from the size of the first area of the first portion, and the second area of the second portion and the fourth area of the fourth portion are equal in size; and according to a third possibility, the third area of the third portion has a size which is different from the size of the first area of the first portion, and the fourth area of the forth portion has a size which is different from the size of the second area of the second portion.

It should be pointed out in this connection, that under the expression "color stimulus specification", the optical impression of a color to a viewer is understood.

By performing a method, in which at least two measurements with differing illumination areas and/or differing measuring areas are performed, and in which a correction value is calculated on the basis of reference value measured on reference objects, by means of which the measurement values are corrected to determine the color stimulus specification under consideration of the translucency thereof, the color stimulus specification of a translucent object under test can be determined with much higher accuracy than it was possible up to now.

To express it even more simpler: The basic principle of the method according to the invention is to perform at least two measurements, whereby either the size of the illuminated portion of the surface of the object under test or the portion whose reflectance is measured or both portions is/are varied between the two measurements. Obtained is a dimension which is a function of the translucency of the object under test. On the other hand, a similar dimension belonging to translucent reference objects is available. By suitably combining these two dimensions, the correct color stimulus specification can be calculated with high accuracy.

A further problem during the determination of the color stimulus specification of the object under test is the ambient light. In practice, ambient light penetrates the object under test, and therefrom, gets into the measuring system. It is understood that the measurement result is distorted by this ambient light. According to a preferred embodiment of the method of the invention, the influence of the ambient light is taken into account by the step of performing a further measurement of the object under test without any illumination at all and by considering the thereby obtained measurement value during calculating the final color stimulus specification.

According to a second aspect, the invention provides an apparatus for determining the color stimulus specification of translucent objects. Again, basically, three slightly different embodiments of the apparatus can be realized. In each of the three embodiments, the apparatus comprises a light emitting element for illuminating the object under test, an optical element for receiving the light reflected by the object under test which is illuminated by the light emitting element, a sensor for measuring the light received by the optical element, and a microprocessor for evaluating the measurement data.

According to the first embodiment, the light emitting element comprises at least two light sources. A first light source illuminates a first portion of the object under test, and a second light source illuminates a second portion of the object under test. The first portion has a size which is different from the size of the second portion.

According to the second embodiment, the optical element comprises at least two lenses. A first lens receives the light reflected by a third portion of the object under test, and a second lens receives the light reflected by a fourth portion of the object under test. Thereby, the third portion has a size which is different from the size of the fourth portion.

According to the third embodiment, the light emitting element comprises at least two light sources and the optical element comprises at least two lenses. A first light source illuminates a first portion of the object under test, and a second light source illuminates a second portion of the object under test. The first portion has a size which is different from the size of the second portion. The first lens receives the light reflected by a third portion of the object under test, and a second lens receives the light reflected by a fourth portion of the object under test. The third portion has a size which is different from the size of the fourth portion.

BRIEF DESCRIPTION OF THE DRAWINGS

In the following, an embodiment of the invention will be further described, with reference to the accompanying drawings, in which:

FIG. 2 shows a schematic illustration of an illuminating and light receiving system of the apparatus shown in FIG. 1;

FIG. 2a shows the two surface portions of an object under test illuminated by the illuminating system of the apparatus shown in FIG. 2;

FIG. 2b shows a sectional view of the probe head, taken along the line A—A in FIG. 2;

DETAILED DESCRIPTION OF A PREFERRED EMBODIMENT

Figure 1:
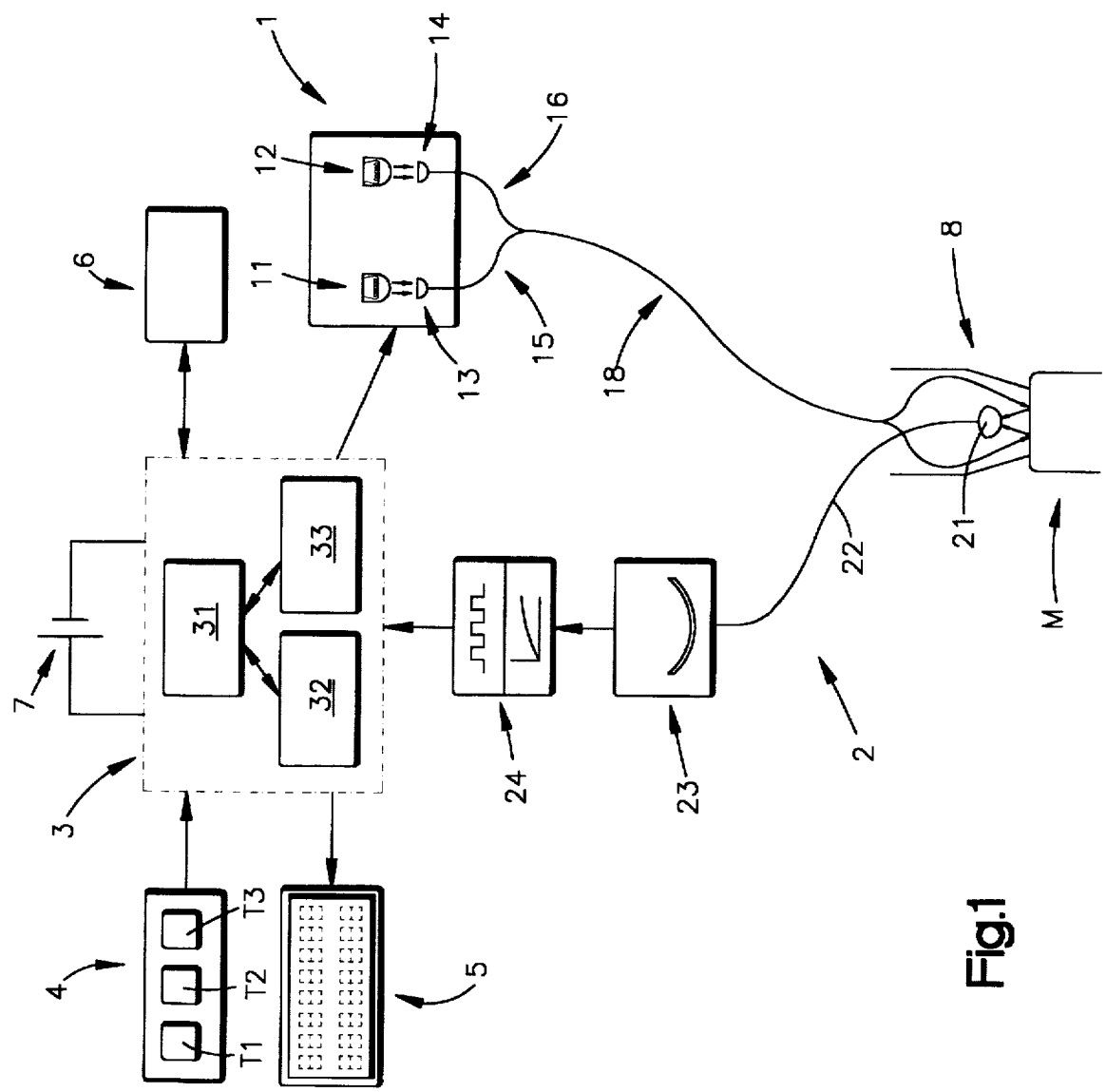
FIG. 1 shows a schematic diagram of an apparatus for determining the color stimulus specification of a translucent object.

With reference to FIG. 1, the general design of an apparatus for determining the color stimulus specification of a translucent object according to the present invention shall be further explained. Essentially, the apparatus comprises an illumination subassembly 1, a light detection subassembly 2, a data processing unit 3, a keyboard 4, a display 5, a serial interface 6 as well as a power supply 7. The object under test, i.e. the object of which the color stimulus specification has to be determined, is designated by reference sign M.

The illumination subassembly 1 for illuminating selected surface portions of the object under test essentially comprises two light sources 11 and 12, two light conducting fiber bundles 15 and 16 and two lenses 13 and 14 which optically couple the light emitted by the two light sources 11 and 12 to the optically conducting fiber bundles 15 and 16. The light detection subassembly 2 is provided for receiving the light reflected by the surface of the object under test M and essentially comprises a lens 21, an associated light conductor 22, a spectrometer 23 and a analog-digital converter module 24. The data processing unit 3 comprises a microprocessor 31 with associated random access memory module 32 and read-only memory module 33. The keyboard 4 comprises a plurality of keys T1, T2, T3 ... for controlling the apparatus. The display unit 5 preferably comprises an alphanumeric LCD module. As an interface, preferably a standard serial interface 6 is provided. For supplying power to the apparatus, a battery 7 is provided.

FIG. 2 shows schematically and in a larger scale the principal design of the illumination subassembly 1, together with the lens 21 and the associated light conductor 22. The light conducting fiber bundles serving for the illumination of the surface of the object under test are shown in a longitudinal sectional view.

For creating two illuminated surface portions having different areas on the surface of the object under test, there is provided an assembly of optically conducting fibers 18 which is designed as follows:

The assembly of optically conducting fibers 18 has a light entry end, shown at the top side in FIG. 2. In the region of this end, the assembly of optically conducting fibers 18 consists of two separate legs of light conducting fiber bundles 15 and 16. The first light conducting fiber bundle 15 comprises a plurality of fibers 15a and the second light conducting fiber bundle 16 comprises a plurality of fibers 16a. The two separate legs, i.e. the light conducting fiber bundles 15 and 16, are united to form a common strand 17 shortly behind the two light sources 11 and 12. In this strand 17, the individual fibers 15a and 16a of the two light conducting fiber bundles 15 and 16 are physically twisted and located in such a way that the different fibers 15a and 16a are distributed over the cross section of the strand 17 as uniformly as possible.

At the other end of the assembly of optically conducting fibers 18, i.e. at the end remote from the above mentioned light entry end, the individual fibers 15a and 16a are separated from each other and arranged in an annular array to form an annularly shaped bundle 19 of optically conducting fibers. The individual fibers 15a and 16a are uniformly distributed over the annular end face of the bundle 19. In this end region of the assembly of optically conducting fibers 18, the annularly arranged fibers 15a and 16a are fixed in a probe head 8. Moreover, the optically conducting fibers 15a and 16a are aligned in the probe head 8 such that the virtual extension of the central longitudinal axes of the optically conducting fibers 15a and 16a intersect essentially in a plane lying in the frontal end face of the probe head 8; in other words, the light emitted by the optically conducting fibers 15a and 16a is focused in the above mentioned plane.

In order to more clearly illustrate the distribution of the individual optically conducting fibers 15a and 16a in the probe head 8, reference is made to FIG. 2b in which there is shown an enlarged cross sectional view of the probe head, taken along the line A—A in FIG. 2. It is understood that the illustration of FIG. 2b is purely schematic and serves for showing the distribution of the individual fibers 15a and 16a in the probe head 8 only; in practice, a much higher number of optically conducting fibers 15a and 16a will be used.

As light sources, there are provided two incandescent lamps 11 and 12, each of which being optically coupled to the associated light conducting fiber bundle 15 and 16, respectively, by means of a lens 13 and 14, respectively. In the case of the first light conducting fiber bundle 15, the light enters under an angle $\alpha$ of approximately 20°, while in the case of the second light conducting fiber bundle 16, the light enters under an angle $\beta$ of approximately 60°. In order to realize such different light entry angles, particularly two methods can be used in practice:

1. Use is made of optically conducting fibers 15a, 16a which have different optical acceptance angles.
2. In front of the entry side of the optically conducting fiber bundle, a lens is arranged, as is shown in the present example by providing the lenses 13 and 14.

It is understood that both methods can be combined, if appropriate.

If the left lamp 11, as shown in FIG. 2, is activated, which sends light to the light conducting fibers 15a under an angle $\alpha$ of approximately 20°, a light spot L1 is created on the surface of the object under test M which has a diameter d1 (FIG. 2a). By activating the right lamp 12, as shown in FIG. 2, a light spot L2 is created on the surface of the object under test M which has a diameter d2 (FIG. 2a). It can be clearly seen that the diameter d1 of the light spot L1 is considerably smaller than the diameter d2 of the light spot L2. Thus, with such an illumination subassembly, using an optically conducting fiber bundle 17 as herein before described, it is possible to create two coaxial light spots L1 and L2 on the surface of the object under test, which have different diameters.

For capturing the light reflected by the illuminated areas of the surface of the object under test M, the probe head 8 is provided with a lens 21 located in the center of the probe head. This lens 21 is optically coupled to a further optically conducting fiber bundle 22 which leads to the spectrometer 23 (FIG. 1). It is understood that this optically conducting fiber bundle 22 is shown in the drawings but in a schematic illustration.

The probe head 8 simultaneously acts as a distance piece, inasmuch as its front end face projects beyond the annular end portion of the light conducting fiber bundle 19 and the lens 21. In this way, the end portion of the light conducting fiber bundle 19 and the lens 21 have a predetermined distance to the surface of the object under test M if the probe head 8 contacts the surface.

If the apparatus according to the invention is used for determining the color stimulus specification of teeth, it is understood that it must be designed quite small. In practice, the probe head 8 could have a diameter in the region of 6–9 mm.

In the following, the basic mode of operation of the above described apparatus will be further explained, with reference to FIGS. 1, 2 and 2a. Since the basic mode of operation of a microprocessor and is associated components is well known to any person skilled in the art, only the characteristics are further explained which are essential in connection with the present invention.

In a first step, reference data are gathered. For this purpose, and using the apparatus according to the invention, a measurement is performed with an opaque reference object as an object under test. In particular, the probe head 8 is contacted with the reference object and the measurement is started by operating a start key T1 of the keyboard 4. During the measurement, the two lamps 11 and 12 are activated one after the other, such that the reference object is illuminated firstly with the first spot L1 having a smaller diameter d1 and thereafter with the second spot L2 having a greater diameter d2. Via the lens 21 and the light conductor 22 coupled thereto, the reflected light is picked up and sent to the spectrometer 23, where, in a manner known per se, it is divided into its spectral components and converted into corresponding analog signals. These analog signals are digitized in the A/D-converter 24 and stored in the memory module 32 of the data processing unit 3. In this way, two reference measurement values are created, i.e. a first reference value a obtained from the measurement with the smaller spot L1 and a second reference value b obtained from the measurement with the greater spot L2.

It is understood that these reference measurements can be performed locally and temporarily independently from the real measurement of an object under test whose color stimulus specification has to be determined. On the one hand, these reference measurements serve for calibrating the apparatus; on the other hand, the inevitable aging of certain components of the apparatus can be compensated for if a reference measurement is performed from time to time.

After these reference measurements have been made, the real measurement of the color stimulus specification of an object M to be tested can be done, i.e. any number of measurements on a plurality of different objects to be tested can be done. As soon as the probe head 8 has approached the object under test M, the measurement is initiated by operating the measurement start key T2 of the keyboard 4. Thereby, three consecutive measurements are performed. The first and second measurements correspond to the ones performed on the reference object, inasmuch as the object under test is illuminated with two differently sized light spots L1 and L2 and the measured values are evaluated and stored as has been described herein before. In this way, a third measurement value c and a fourth measurement value d is obtained. The third measurement is done without illuminating the object under test M. In this way, a fifth measurement value e is obtained which is proportional of the ambient illumination.

On the basis of these five measurements, which all are spectral measurements, i.e. functions of the wave length $f(\lambda)$, the correct remission spectrum $R(\lambda)$ can be calculated, i.e. that remission spectrum $R(\lambda)$, which one would have obtained if the object under test had been illuminated by means of a light spot with infinite size. In particular:

The influence of the ambient light is subtracted from the measurement values c and d:

$$c1(\lambda)=c(\lambda)-e(\lambda)$$

$$d1(\lambda)=d(\lambda)-e(\lambda);$$

The varying luminance of the illumination is corrected, by dividing through the reference values:

$$c2(\lambda)=c1(\lambda)/a(\lambda)$$

$$d2(\lambda)=d1(\lambda)/b(\lambda)$$

Thereafter, a correction corresponding to the light loss due to translucency is added to the remission data $d2(\lambda)$:

$$d3(\lambda)=d2(\lambda)+f(d2(\lambda),c2(\lambda));$$

Now, The remission data $d3(\lambda)$ are multiplied with the remission data of the reference object:

$$R(\lambda)=d3(\lambda) \cdot R_{REF}(\lambda).$$

On the basis of the remission data $R(\lambda)$, the correct color stimulus specification of the object under test can be evaluated; the method therefor is well known to any person skilled in the art.

The remission data of the reference object have previously been measured, for example by the manufacturer of the apparatus during the calibration, with the help of an arbitrary remission spectrophotometer, and have been stored in a memory module of the apparatus. Moreover, the function f(d2,c2) has previously been determined, e.g. by the manufacturer of the apparatus, by storing the measurement values of many different reference objects with varying remission data and varying translucency in a memory module of the apparatus. In practice, such reference objects are measured first with a light spot having a diameter d1, then with a light spot having a different diameter d2, and finally with a light spot having a diameter as large as possible, and the measurement values are stored in the memory module. The measurement value obtained during the measurement with the third large light spot corresponds to the function value f(d2,c2). The particular function values can, thereafter, stored in a memory module of the apparatus in the form of a table.

In the case of measuring the color of teeth and of determining of the correct composition of a denture, respectively, the previously mentioned reference dentures are measured with the apparatus according to the invention in order to be in a position to select the composition with matches best. This can be done either by the manufacturer of the apparatus or by the operator of the apparatus himself. The color stimulus specifications of the reference dentures, then, are stored in a memory module of the apparatus. After having measured a natural tooth, the apparatus is easily in a position to select that reference denture out of a plurality of reference dentures, whose color stimulus specification matches the color stimulus specification of the measured natural tooth best, i.e. to select that reference denture, which has the least color difference compared with the natural tooth. The calculation of the color difference, again, is disclosed in the prior art and well known to a skilled person.

Via the serial interface 6 of the apparatus, it is possible not only to read data, but also to write data. For example, the apparatus could be operated by means of a personal computer via the serial interface 6, and the gathered measurement values could be sent to a printer by means of the personal computer. If desired, it could also be possible to input correction values via the serial interface 6 to the apparatus.

It should be pointed out that a great number of variations of the method according to the invention is possible within the scope of the present invention. The same is true with reference to the apparatus herein before described as an exemplary embodiment only. For example, the light sources could be located directly in the probe head. Instead of light sources with an associated optical element to limit the angle of the light beam hitting the input end of the light conducting fiber bundle, it is possible to make use of light conducting fiber bundle whose fibers have different light acceptance angles. Moreover, it is possible, for instance, to make use of a light conducting fiber bundle consisting of fibers with three different light acceptance angles or being illuminated under three different angles; consequently, three measurements with three differently sized light spots would have to be performed.

Figure 3:
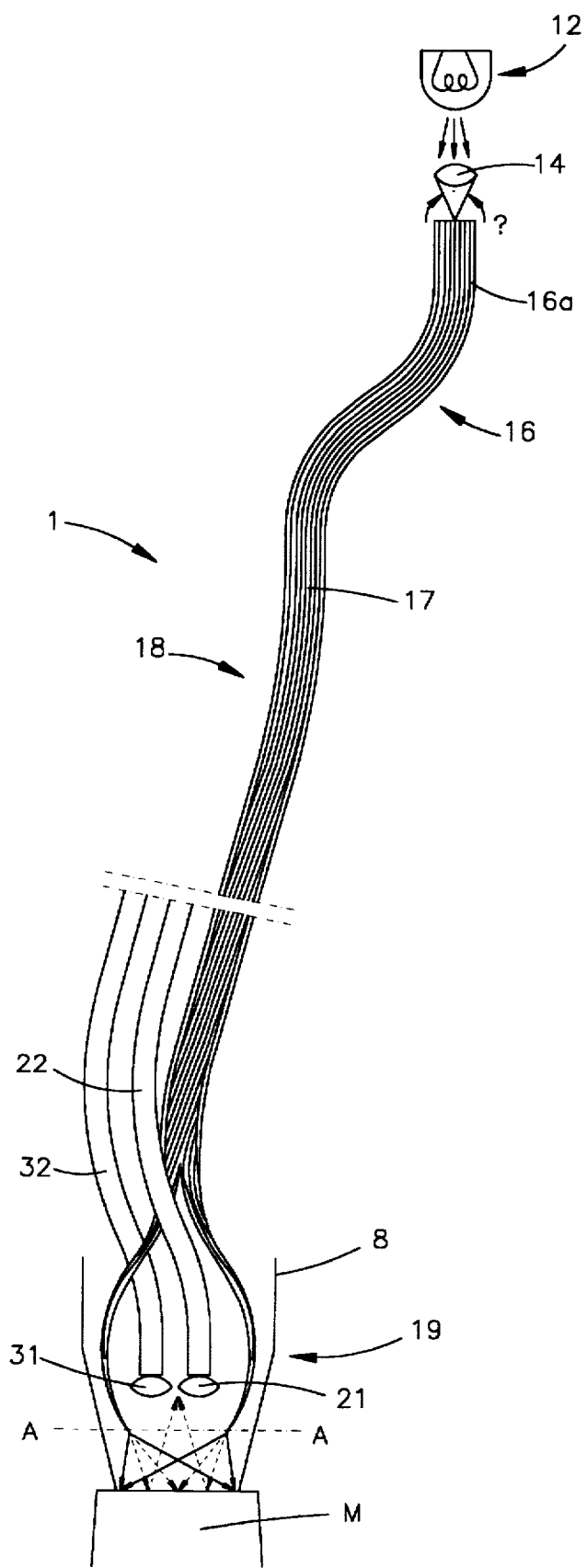
FIG. 3 is a view similar to FIG. 2 illustrating a second embodiment of the present invention.
Figure 4:
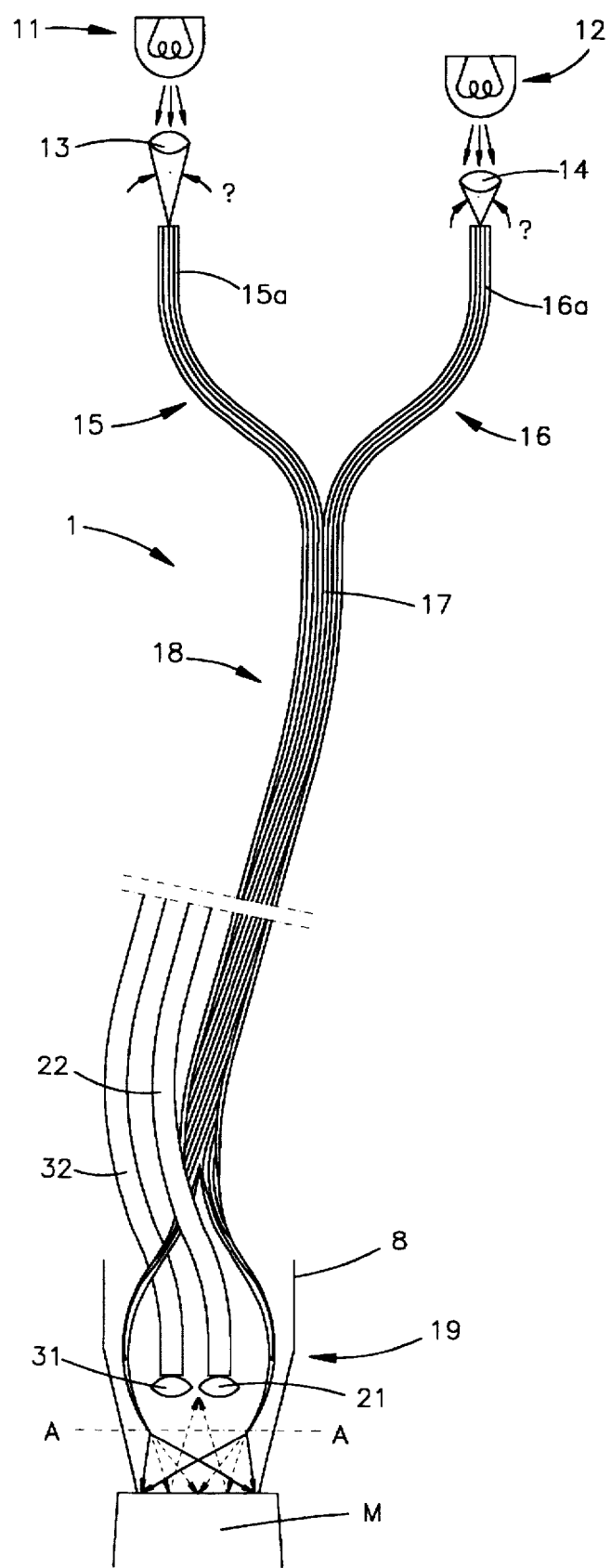
FIG. 4 is a view similar to FIG. 3 illustrating a third embodiment of the present invention.

The entire illumination subassembly and detection subassembly could be inverted as shown in FIG. 3; inasmuch as the object under test is illuminated by one light spot having a predetermined size only, whereby the measurement of the light reflected by the surface of the object under test would have to be done under two or more different angles of acceptance. For this purpose, two independent optical lenses 21 and 31 could be used, having different optical characteristics. It could also be imagined to use, in the last mentioned case, only one optical lens in conjunction with suitable mechanical means which offer the possibility to vary the size of the surface portion to be measured. Finally, as a further variation of the method is illustrated in FIG. 4, it is possible to use two light sources 11 and 12 for creating two light spots on the surface of the object under test with different size, and simultaneously to use two light detection means comprising optical lenses 21 and 31, having different optical characteristics, coupled to optically conducting fiber bundles 22 and 32, respectively, which measure the reflected light under different angles.

If the apparatus according to the invention is to be used in the dental field in order to determine the color of a denture to be used with an individual person, it is preferred to measure the color stimulus specification of the two teeth which are adjacent to the denture to be inserted, to evaluate a mean value and to show that mean value in the display of the apparatus.

What is claimed is:

1. A method for determining the color stimulus specification of translucent objects, in which the surface of the object under test is partially illuminated and the light reflected by a selected portion of the surface of the object under test is measured and arithmetically evaluated, the method comprising the steps of:

(i) in a first measurement, illuminating a first portion of said surface of the object under test, said first portion having a first area, and measuring the light reflected by a second portion of said surface of the object under test, said second portion having a second area, thus obtaining a first set of measurement values;

(ii) in a second measurement, illuminating a third portion of said surface of the object under test, said third portion having a third area, and measuring the light reflected by a fourth portion of said surface of the object under test, said fourth portion having a fourth area, thus obtaining a second set of measurement values;

(iii) providing a set of reference measurement values obtained from the measurement of a reference object and calculating first and second sets of compensated measurement values, said first and second sets of compensated measurement values being functions of said first and second sets of measurement values and said reference measurement values;

(iv) calculating an intermediate reflection value as a function of said first and second sets of compensated measurement values and a correction value which corresponds to the light loss caused by the translucency of the object under test; and (v) calculating a final reflection value as a function of said intermediate reflection value and the known reflection values of said reference object to obtain from said final reflection value the color stimulus specification of said object under test;

said first area of said first portion and said third area of said third portion being equal in size, and said fourth area of said forth portion having a size which is different from the size of said second area of said second portion.

2. A method for determining the color stimulus specification of translucent objects, in which the surface of the object under test is partially illuminated and the light reflected by a selected portion of the surface of the object under test is measured and arithmetically evaluated, the method comprising the steps of:

(i) in a first measurement, illuminating a first portion of said surface of the object under test, said first portion having a first area, and measuring the light reflected by a second portion of said surface of the object under test, said second portion having a second area, thus obtaining a first set of measurement values;

(ii) in a second measurement, illuminating a third portion of said surface of the object under test, said third portion having a third area, and measuring the light reflected by a fourth portion of said surface of the object under test, said fourth portion having a fourth area, thus obtaining a second set of measurement values;

(iii) providing a set of reference measurement values obtained from the measurement of a reference object and calculating first and second sets of compensated measurement values, said first and second sets of compensated measurement values being functions of said first and second sets of measurement values and said reference measurement values;

(iv) calculating an intermediate reflection value as a function of said first and second sets of compensated measurement values and a correction value which corresponds to the light loss caused by the translucency of the object under test; and (v) calculating a final reflection value as a function of said intermediate reflection value and the known reflection values of said reference object to obtain from said final reflection value the color stimulus specification of said object under test;

said third area of said third portion having a size which is different from the size of said first area of said first portion, and said second area of said second portion and said fourth area of said fourth portion being equal in size.

3. A method for determining the color stimulus specification of translucent objects, in which the surface of the object under test is partially illuminated and the light reflected by a selected portion of the surface of the object under test is measured and arithmetically evaluated, the method comprising the steps of:

(i) in a first measurement, illuminating a first portion of said surface of the object under test, said first portion having a first area, and measuring the light reflected by a second portion of said surface of the object under test, said second portion having a second area, thus obtaining a first set of measurement values;

(ii) in a second measurement, illuminating a third portion of said surface of the object under test, said third portion having a third area, and measuring the light reflected by a fourth portion of said surface of the object under test, said fourth portion having a fourth area, thus obtaining a second set of measurement values;

(iii) providing a set of reference measurement values obtained from the measurement of a reference object and calculating first and second sets of compensated measurement values, said first and second sets of compensated measurement values being functions of said first and second sets of measurement values and said reference measurement values;

(iv) calculating an intermediate reflection value as a function of said first and second sets of compensated measurement values and a correction value which corresponds to the light loss caused by the translucency of the object under test; and (v) calculating a final reflection value as a function of said intermediate reflection value and the known reflection values of said reference object to obtain from said final reflection value the color stimulus specification of said object under test;

said third area of said third portion having a size which is different from the size of said first area of said first portion, and said fourth area of said forth portion having a size which is different from the size of said second area of said second portion.

4. A method according to one of the claims 1–3, further comprising the step of, in a third measurement, illuminating a fifth portion of said surface of the object under test, said fifth portion having a fifth area, and measuring the light reflected by a sixth portion of said surface of the object under test, said sixth portion having a sixth area, thus obtaining a third set of measurement values, whereby said third set of measurement values is correspondingly taken into account in said steps (iii), (iv) and (v).

5. A method according to one of the claims 1–3, further comprising the step of, in a further measurement, exposing said surface of the object under test to ambient light conditions and measuring the light reflected by a portion of said surface of the object under test, thus obtaining a third set of measurement values, whereby said third set of measurement values is correspondingly taken into account in said steps (iii), (iv), and (v).

6. A method according to one of the claims 1–3, in which said reference measurement values are obtained, in a first reference measurement, by illuminating a fifth portion of the surface of an opaque reference object, said fifth portion having a fifth area, and measuring the light reflected by a sixth portion of said surface of said reference object, said sixth portion having an sixth area, and, in a second reference measurement, by illuminating a seventh portion having a seventh area, and measuring the light reflected by a eighth portion of sa id surface of the object under test, said eighth portion having a eighth area, at least one of said fifth, sixth, seventh and eighth areas being different from the remaining ones.

7. A method for determining the color stimulus specification of translucent objects, in which the surface of the object under test is partially illuminated and the light reflected by a selected portion of the surface of the object under test is measured and arithmetically evaluated, the method comprising the steps of:

in a first measurement, illuminating a first portion of the surface of an opaque reference object, measuring the amount of light reflected by said first portion of the surface of said reference object and storing the measurement result as a first reference value;

in a second measurement, illuminating a second portion of the surface of said opaque reference object, said second portion of the surface of said reference object being bigger or smaller than said first portion of the surface of said reference object, measuring the amount of light reflected by said second portion of the surface of said reference object and storing the measurement result as a second reference value;

in a third measurement, illuminating a first portion of the surface of an object under test, measuring the amount of light reflected by said first portion of the surface of said object under test and storing the measurement result as a first temporary measurement value;

in a fourth measurement, illuminating a second portion of the surface of said object under test, said second portion of the surface of said object under test being bigger or smaller than said first portion of the surface of said object under test, measuring the amount of light reflected by said second portion of the surface of said object under test and storing the measurement result as a second temporary measurement value;

in a fifth measurement, exposing said surface of said object under test to ambient light conditions and measuring the light reflected by a portion of said surface of said object under test, thus obtaining a third measurement value;

arithmetically subtracting said third measurement value from said stored first temporary measurement value to obtain a first definitive measurement value, and arithmetically subtracting said third measurement value from said stored second temporary measurement value to obtain a second definitive measurement value;

arithmetically dividing said first definitive measurement value by said stored first reference value to obtain a first compensated measurement value, and arithmetically dividing said second definitive measurement value by said stored second reference value to obtain a second compensated measurement value;

calculating an intermediate reflection value as a function of said first and second compensated measurement values and a correction value which corresponds to the light loss caused by the translucency of said object under test; and calculating a final reflection value as a function of said intermediate reflection value and the known reflection values of said reference object to obtain from said final reflection value the color stimulus specification of said object under test.

8. A method according to one of the claims 1, 2, 3 or 7, further comprising the steps of:

providing a table containing a plurality of color stimulus specification values obtained from measuring a plurality of different translucent reference objects;

comparing said arithmetically calculated color stimulus specification of said object under test with the values contained in said table;

determining the color stimulus specification value of said table which is closest to said arithmetically calculated color stimulus specification of said object under test; and optically displaying said closest color stimulus specification value.

9. A method according to one of the claims 1, 2, 3 or 7, in which said translucent objects are human teeth and said reference objects are dentures.

10. A method of selecting a denture having a desired color stimulus specification which matches the color stimulus specification of a human tooth, comprising the steps of determining the color stimulus specification of a tooth which is closest to the tooth to be replaced by a denture using a method according to one of claims 1, 2, 3, or 7, displaying the color stimulus specification of said tooth which has been measured, and selecting that denture from a group of dentures with different color stimulus specifications which has the closest color stimulus specification.

11. A method of selecting a denture having a desired color stimulus specification which matches the color stimulus specification of a human tooth, comprising the steps of determining the color stimulus specification of the two teeth which are adjacent to the tooth to be replaced by a denture using a method according to one of claims 1, 2, 3 or 7, displaying the color stimulus specifications of said teeth which have been measured, and selecting that denture from a group of dentures with different color stimulus specifications which ahs the closest color stimulus specification.

12. An apparatus for determining the color stimulus specification of translucent objects, comprising a light emitting means for illuminating the object under test, an optical means for receiving the light reflected by the object under test which is illuminated by said light emitting means, a sensor means for measuring the light received by said optical means, and a microprocessor means for evaluating the measurement data, said light emitting means comprising at least two light sources, a first light source of said at least two light sources illuminating a first portion of said object under test, and a second light source of said at least two light sources illuminating a second portion of said object under test, said first portion having a size which is different from the size of said second portion.

13. An apparatus for determining the color stimulus specification of translucent objects, comprising a light emitting means for illuminating the object under test, an optical means for receiving the light reflected by the object under test which is illuminated by said light received by said optical means, and a microprocessor means for evaluating the measurement data, said optical means comprising at least two lenses, a first lens of said at least two lenses receiving the light reflected by a first portion of said object under test, and a second lens of said at least two lenses receiving the light reflected by a second portion of said object under test, said first portion having a size which is different from the size of said second portion.

14. An apparatus for determining the color stimulus specification of translucent objects, comprising a light emitting means for illuminating the object under test, an optical means for receiving the light reflected by the object under test which is illuminated by said light emitting means, a sensor means for measuring the light received by said optical means, and a microprocessor means for evaluating the measurement data, said light emitting means comprising at least two light sources, a first light source of said at least two light sources illuminating a first portion of said object under test, and a second light source of said at least two light sources illuminating a second portion of said object under test, said first portion having a size which is different from the size of said second portion, and said optical means comprising at least two lenses, a first lens of said at least two lenses receiving the light reflected by a third portion of said object under test, and a second lens of said at least two lenses receiving the light reflected by a fourth portion of said object under test, said third portion having a size which is different from the size of said fourth portion.

15. An apparatus according to claim 12 or 14, in which at least a part of said light emitting means and of said light receiving means is located in a probe head means, and in which said light emitting means comprises at least two sets of light conducting fibers having different light acceptance angles and/or which are illuminated under different angles.

16. An apparatus according to claim 12 or 14, in which said light emitting means comprises two light sources, each of which is optically coupled with a light conducting fiber bundle incorporating a plurality of single light conducting fibers, said two light conducting fiber bundles being united to a single leg at a location behind said two light sources and said leg being opened up to form an annular end portion at a location situated in the interior of said probe head means to form an evenly distributed annular light source.

17. An apparatus according to claim 15, in which said light receiving means is located centrally in said probe head means.

18. An apparatus according to claim 12 or 14, in which each of said two light sources is provided with a lens means, whereby the light emitted from said first light source and received by one of said two light conducting fiber bundles is focused by one of said two lenses to hit the end face of said one of said two light conducting fiber bundles under a first angle of incidence, and whereby the light emitted from said second light source and received by the other of said two light conducting fiber bundles is focused by the other of said two lenses to hit the end face of the other of said two light conducting fiber bundles under a second angle of incidence which is different from said first angle of incidence.

19. An apparatus according to claim 17, in which said probe head means is designed as distance piece, whereby its front end projects beyond said annular end portion of said light conducting fiber bundle.

20. An apparatus according to claim 19, in which the light emitted by said evenly distributed annular light source is focused in a plane coinciding with the front end plane of said probe means.

21. An apparatus according to one of the claims 12–14, further comprising electronic memory module means for storing reference values and/or correction values.

22. An apparatus according to one of the claims 12–14, further comprising an alphanumeric display means for displaying the measurement results and/or an identification of a reference denture having a color stimulation specification closest to the one of the object under test.

* * * * *